United States Patent [19]

Andersen et al.

[11] Patent Number: 4,937,046

[45] Date of Patent: Jun. 26, 1990

[54] STERILIZATION SYSTEM AND METHOD

[75] Inventors: Harold W. Andersen; William K. Anderson, both of Oyster Bay, N.Y.; Charles H. Harrison, Haw River, N.C.

[73] Assignee: H. W. Andersen Products Inc., Oyster Bay, N.Y.

[21] Appl. No.: 148,408

[22] Filed: Jan. 26, 1988

[51] Int. Cl.$^5$ .............................................. A61L 2/20
[52] U.S. Cl. .......................................... 422/34; 422/1; 422/33; 422/294
[58] Field of Search ........................... 422/34, 28, 1–2, 422/294, 33

[56] References Cited

U.S. PATENT DOCUMENTS

| | | | |
|---|---|---|---|
| 3,107,974 | 10/1963 | Potapenko | 422/4 |
| 3,399,955 | 9/1968 | Zimmerman | 422/28 |
| 3,476,506 | 11/1969 | Andersen et al. | 422/34 X |
| 3,598,517 | 8/1971 | Beecher | 422/34 X |
| 3,600,127 | 8/1971 | Kereluk et al. | 422/34 X |
| 3,716,961 | 2/1973 | Cope et al. | 422/34 X |
| 4,130,393 | 12/1978 | Fox | 422/34 X |
| 4,410,492 | 10/1983 | Kaye | 422/34 X |
| 4,435,194 | 3/1984 | Picard et al. | 422/29 X |
| 4,461,097 | 7/1984 | Thornton | 422/34 X |

Primary Examiner—Barry S. Richman
Assistant Examiner—Amalia L. Santiago
Attorney, Agent, or Firm—Jordan and Hamburg

[57] ABSTRACT

Apparatus and method for sterilizing articles includes a sealed first enclosure made at least partially of a gas-permeable plastic film and a sealed container releasably containing a gaseous sterilant under pressure, the container being enclosed within the first enclosure. An openable second enclosure made at least partially of a gas-permeable plastic film is also provided and the first enclosure and the articles to be sterilized are disposed in the second enclosure. The sterilant which is characterized by toxicity and flammability when released from its container diffuses from the first enclosure into the second enclosure at a rate capable of establishing sterilization conditions in the second enclosure during a sterilization cycle to thereby effect sterilization of the articles in the second enclosure. A third enclosure is also provided in which the second enclosure containing the articles to be sterilized is disposed. A flushing system introduces air into the second enclosure to flush out the sterilizing gas therein into the third enclosure during a flushing cycle following completion of the sterilization cycle, and an exhaust system exhausts the sterilant gas and air from the third enclosure during the flushing cycle and conducts the exhausted sterilant gas and air to a remote area, whereby the flushing system and the exhaust system minimize the extent of residue sterilant gas in the work area surrounding the apparatus.

19 Claims, 2 Drawing Sheets

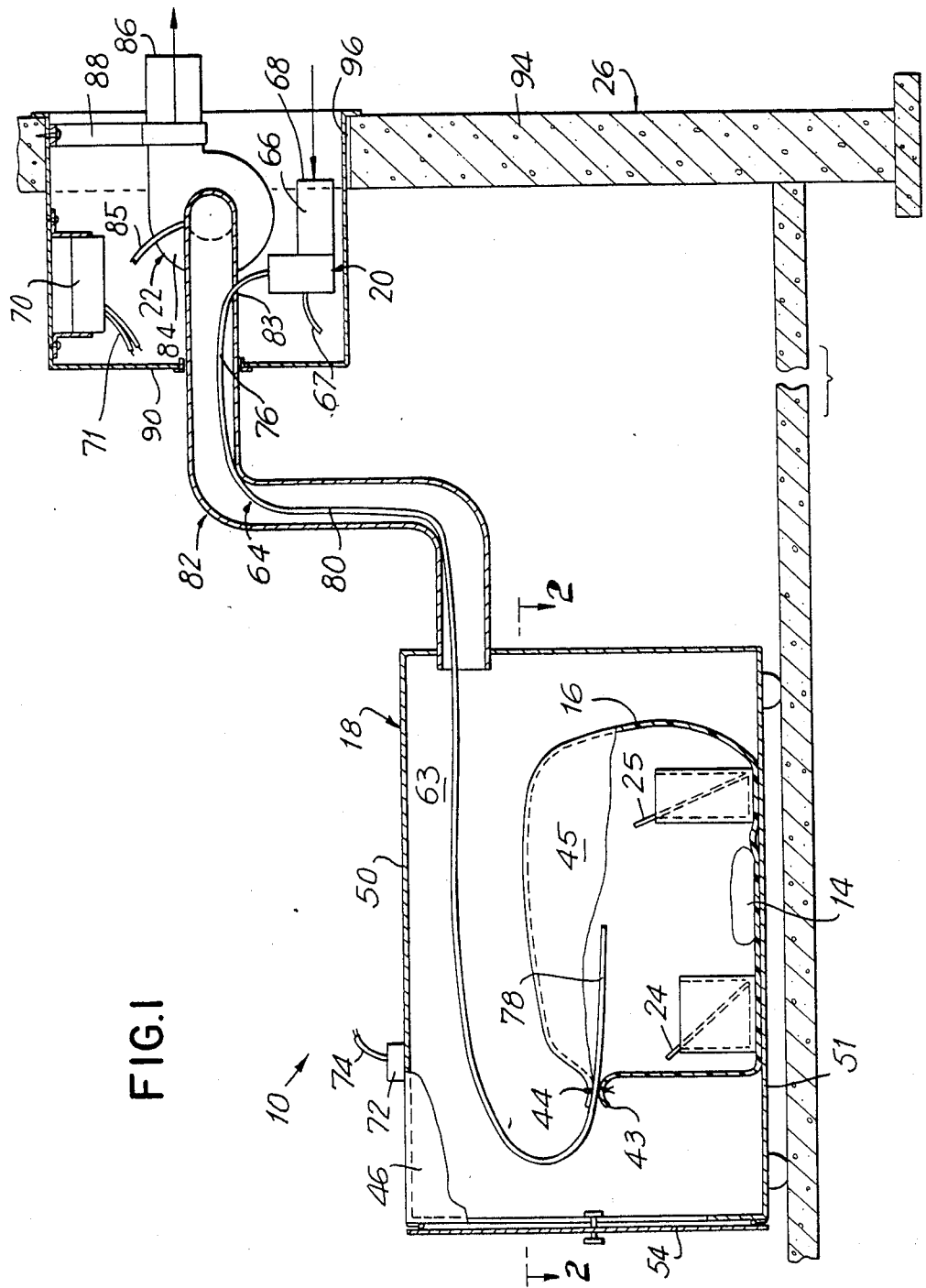

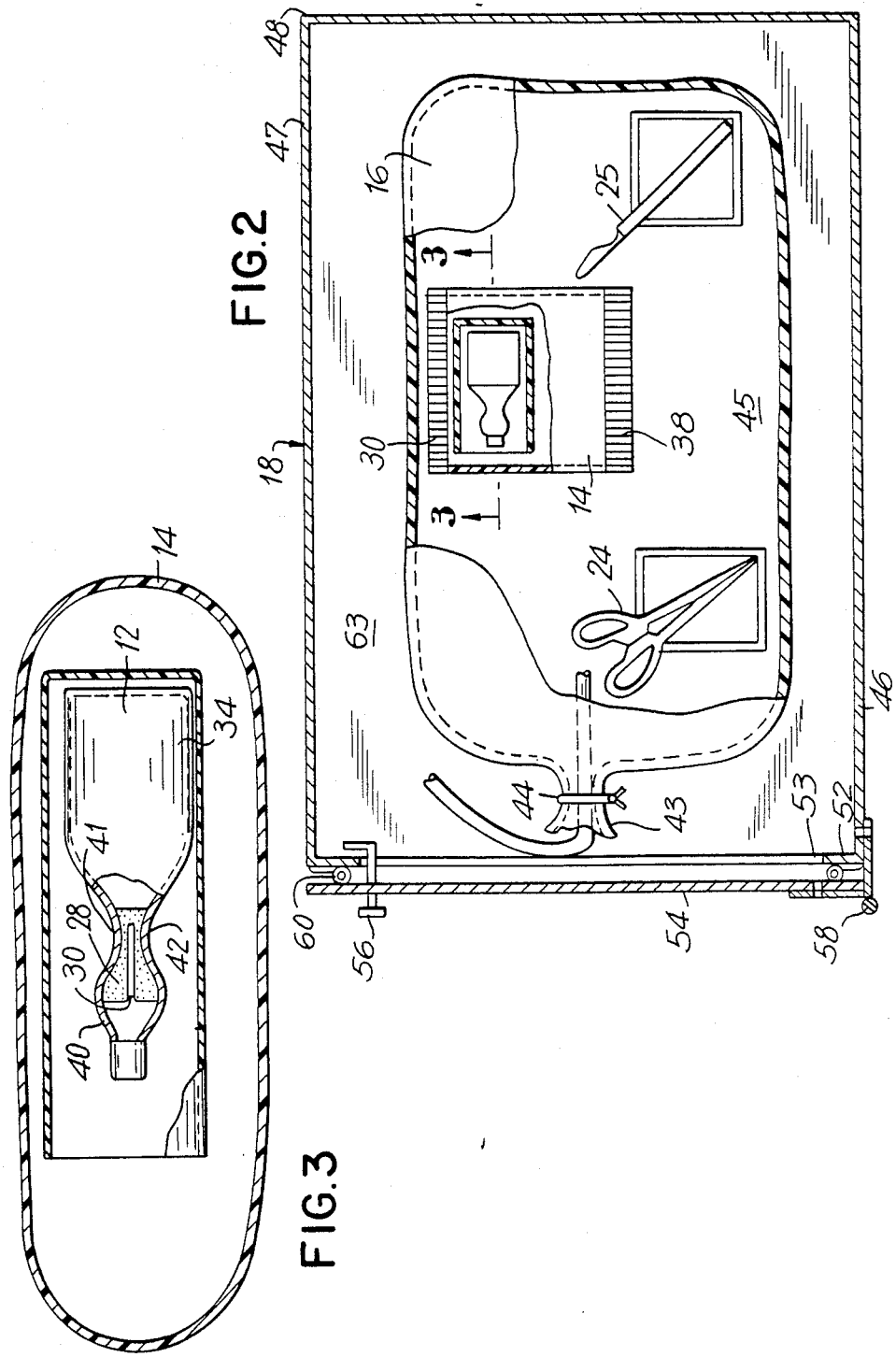

STERILIZATION SYSTEM AND METHOD

The invention relates to a sterilization system and particularly to a sterilization system having a post sterilizing flush cycle.

BACKGROUND OF THE INVENTION

A prior art sterilization system is described in U.S. Pat. No. 3,476,506, issued Nov. 4, 1969. This prior art patent discloses an ampule or source of sterilant, a gas release bag which contains the ample, a liner bag which contains the gas release bag and the items to be sterilized, and a metal container which contains the liner bag. Ethylene oxide sterilizing gas from the ampule is released into the gas release bag and the sterilization gas in the gas release bag is released into the liner bag to sterilize items within the liner bag. After a period of time (e.g. 4 hours), virtually all of the gas that is contained within the ampule is diffused from the inside of the gas release bag into the liner bag, where it is held in contact with the items to be sterilized for the duration of the sterilizing cycle (e.g. 12 hours). During this time, a significant portion of the gas is gradually released by the liner bag gas diffusion membrane into the space between the liner bag and the metal container. This gas escapes from the unsealed metal container into the ambient work area.

One problem with this prior art sterilization system was that the operator is exposed to the sterilizing gas in the work area and to the gas in the liner bag when the latter is opened upon completion of the sterilization cycle. This problem is overcome in the present invention by utilizing a post sterilization flush which minimizes the extent of residue sterilant in the surrounding work area.

SUMMARY OF THE INVENTION

According to the present invention, an apparatus for sterilizing articles includes a sealed first enclosure made at least partially of a gas permeable plastic film and a sealed container releasably containing a gaseous sterilant under pressure, the container being enclosed within the first enclosure. An openable second enclosure made at least partially of a gas permeable plastic film is also provided and the first enclosure and the articles to be sterilized are disposed in the second enclosure. The sterilant which is characterized by toxicity and flammability when released from its container diffuses from the first enclosure into the second enclosure at a rate capable of establishing sterilization conditions in the second enclosure during a sterilization cycle to thereby effect sterilization of the articles in the second enclosure. A third enclosure is also provided in which the second enclosure containing the articles to be sterilized is disposed. A flushing system introduces air into the second enclosure to flush out the sterilizing gas therein into the third enclosure during a flushing cycle following completion of the sterilization cycle, and an exhaust system exhausts the steriliant gas and air from the third enclosure during the flushing cycle and conducts the exhausted sterilant gas and air to a remote area, whereby the flushing system and the exhaust system minimize the extent of residue sterilant gas in the work area surrounding the apparatus.

The method of the present invention includes the steps of containing a volatile sterilant with a sealed first enclosure made at least partially of a gas permeable membrane, disposing the sealed first enclosure and the items to be sterilized within a second enclosure made at least partially of a gas permeable plastic film, disposing the second enclosure within a third enclosure, effecting a sterilizing cycle by releasing the sterilant from the first container in gaseous form, passing the gaseous sterilant into the second enclosure by diffusion through the gas permeable membrane, maintaining sterilizing conditions in the second enclosure to effect sterilization of the items to be sterilized in the second enclosure, passing the gaseous sterilant from the second enclosure to the third enclosure by diffusion through the gas permeable film, effecting a flushing cycle subsequent to the sterilizing cycle by introducing air into said second enclosure to flush out the sterilizing gas from the second enclosure into the third enclosure, exhausting the sterilizing gas and air from the third enclosure, and conducting the exhausted sterilizing gas and air to a remote area, whereby the flushing cycle minimizes the extent of residue sterilant gas in the ambiance.

BRIEF DESCRIPTION OF THE DRAWINGS

The above advantages and subsequent description will be more readily understood by reference to the following drawings.

FIG. 1 is a section view as taken through a sterilization system according to the invention;

FIG. 2 is a section view as taken along the line 2—2 of FIG. 1; and

FIG. 3 is a section view as taken along the line 3—3 of FIG. 2.

DESCRIPTION OF THE PREFERRED EMBODIMENTS

Referring to the drawings, there is shown a sterilization system 10 which includes an ampule or source of sterilant 12, a gas release bag 14 in which the sealed ampule is disposed, a liner bag or second enclosure 16 which contains the gas release bag 14 and the items to be sterilized, and a housing or third enclosure 18. System 10 also includes an air supply means or assembly 20 which connects to the liner bag 16 within the housing 18. System 10 also includes an air and gas exhaust means or assembly 22 which connects to the housing 18. Housing 18 is disposed in an enclosure such as a building 26.

The previously-mentioned U.S. Pat. No. 3,476,506, which is incorporated herein by reference more fully describes ampule 12, gas release bag 14 and liner bag 16.

Ampule 12 contains ethylene oxide 34 in a liquid state which escapes into gas release bag 14 when ampule 12 is broken. Ampule 12 also has a sealed portion 32 which is sealed after the ethylene oxide 34 is deposited inside the ampule 12. Ampule 12 is placed inside a protective sleeve 36 after it is filled and sealed.

After ampule 12 is placed in sleeve 36, ampule 12 and sleeve 36 are placed in gas release bag 14. The bag 14 is then sealed or closed, for example by sealing one of its end portions 38 or 39.

Ampule 12 has a spout 40 which has a score line 41 that is located at the narrow neck portion 42 of ampule 12. When required, spout 40 is broken manually, in order to release ethylene oxide gas into the gas release bag 14.

Gas release bag 14 is made of a semi-permeable material, such as a polyethylene film, which releases or diffuses the ethylene oxide 34 at a predetermined rate into the liner bag 16 in order to sterilize instruments 24, 25 inside liner bag 16.

Liner bag 16 has a neck portion 43 which has a twisted wire 44 or other closure for closing neck portion 43. Liner bag 16 has an interior cavity 45 in which gas release bag 14 is placed together with instruments 24, 25.

Housing 18 has side walls 46, 47, a rear wall 48, a top wall 50, a bottom wall 51, and a front wall 52, which has an opening 53 with a door 54. Door 54 has a handle and lock 56 and a hinge 58. A loose fit between the door 54 and the walls of the chamber 63 permits air to leak inwardly to chamber 63. The loose fit provides just enough space for some air to leak into the chamber 63 which is at a pressure less than atmospheric, as will be explained, but not such a large space that the reduced pressure in the chamber 63 cannot be maintained by the exhaust means 22. Alternatively, the loose fit may be dispensed with and the housing may be sealed gas-tight, for example by gasket 60. The housing 18 may be made of metal, e.g. stainless steel.

Chamber 63 is normally maintained at a negative pressure, or less than atmospheric pressure, by exhaust means 22.

Air supply means 20 has an air flush tube 64 and an air pump 66 which has an air inlet opening 68. Air supply means 20 has a timer 70 having a circuit connector 71 and a switch 72 which has a circuit connector 74. Switch 72 is mounted on the housing 18. Air pump 66 has a circuit connector 67 which connects to timer connector 71. Switch connector 74 also connects to timer 70.

Air tube 64 has an end portion 76 which connects to the discharge outlet of air pump 66. Air tube 64 has an opposite end portion 78 which is disposed inside liner bag 16. Air tube 64 has an intermediate portion 80, which extends through housing rear wall 48 and through housing chamber 63 and through neck portion 43 of liner bag 16 to the liner bag cavity 45.

Air and gas exhaust means 22 has an exhaust conduit or hose 82 and an exhaust motor 84 which has an air outlet opening 86. Exhaust motor 84 has a circuit connector 85 which connects to timer 70 for control of exhaust motor 84. Exhaust motor 84 is suitably supported such as by straps 88. Exhaust unit 22 also has a support 90 which supports timer 70, air pump 66 and exhaust pump strap 88.

Intermediate portion 80 of air tube 64 may be disposed within exhaust hose 82. End portion 76 of air tube 64 passes through an opening 83 in exhaust hose 82.

Building 26 may have a wall 94 with a wall opening 96. Wall 94 supports framework 90.

In operation, sterilization is initiated by manually fracturing or breaking off the spout of the glass ampule 12 along the score line 41 preformed around the narrow neck 42 of the ampule. The release bag 14 with the released sterilant is disposed in the liner bag 16 along with the material to be sterilized. The sterilizing gas that is released within the gas release bag 14 is diffused from the gas release bag into the liner bag 16 where it is held in contact with the material to be sterilized for the duration of the sterilizing cycle (e.g. 12 hours). During this time, a significant portion of the sterilizing gas is gradually released from the liner bag 16 into chamber 63 of housing 18. Chamber 63 is maintained at a negative pressure due to the operation of the exhaust motor 84 so that none of the slowly-diffusing gas from the liner bag 16 is allowed to escape into the work space. Thus the sterilizing gas in chamber 63 along with air leaking into chamber 63 about the non-gas-tight door 54 is exhausted through exhaust conduit 82 to exhaust opening 86. At the end of the sterilizing cycle, the air pump 20 is activated to provide a post-sterilization flush cycle. Thus the air pump 20 is activated and fresh air flows through the air flush tube 64 to the interior of the liner bag 16 such that fresh air enters the liner bag 16 to dilute the residual sterilizing gas within the liner bag 16, and when the liner bag 16 is fully inflated, forces the mixture of fresh air and residual sterilizing gas to exit the liner bag 16 at the point where the air supply means enters the liner bag 16, that is, where the air flush tube 64 passes through the mouth of the liner bag 16 and is secured by the twisted wire 44. The use of the twisted wire 44 does not provide a gas-tight seal when the liner bag 16 is fully inflated, such that the mixture of fresh air and residual sterilizing gas exits the liner bag around the non-gas-tight twist closure. The diluted gas mixture in the chamber 63 is exhausted by the exhaust means 22 as previously described.

When the liner bag 16 is eventually opened after completion of the sterilizing cycle and the sterilizing flush cycle, the residual sterilizing gas in liner bag 16 is removed by the exhaust means 22 which continues to operate and it is dissipated harmlessly to the outside atmosphere.

In one embodiment of the system 10, there is a reduction of more than one hundred fold in the residual gas retained by liner bag 16 at the time of opening. For example, the concentration of gas within the liner bag 16 at one end of the twelve-hour sterilizing cycle is 130,000 parts per million in the prior art arrangement without the additional air flush technique. The addition of the air flush technique reduces the residual gas to approximately 1000 ppm within liner bag 16 at the end of the two-hour flush time. With system 10, the escape of ethylene oxide gas into the work space atmosphere is sufficiently low so as to be well below 1 ppm and is typically less than 0.1 ppm.

Exhaust means 22 provides that chamber 63 is at less than atmospheric pressure and assures that none of the slowly diffusing gas in chamber 63 from liner bag 16 is allowed to escape into the work space. When air pump 66 is activated during the flush cycle, fresh air entering liner bag 16 dilutes the residual sterilizing gas within liner bag 16 and, when liner bag 16 is fully inflated, forces the mixture of fresh air and residual sterilizing gas to exit liner bag 16 through liner bag end portion 43 where air tube end portion 78 enters liner bag 16 as previously described. This diluted gas mixture in liner bag 16 is collected by exhaust means 22. Most of the residual gas that might be released when liner bag 16 is opened, after the sterilization and flush cycle is completed, is also removed by exhaust means 22 where it is harmlessly dissipated through exhaust opening 86 to the atmosphere outside wall 94.

System 10 easily meets a recent United States regulation of the allowable work space atmosphere of a maximum of 1 ppm (time weighted average over 8 hours), and easily meets another regulation with a significant incentive of less than 0.5 ppm.

While the invention has been described in its preferred embodiments, it is to be understood that the words which have been used are words of description rather than limitation and that changes may be made within the purview of the appended claims without departing from the true scope and spirit of the invention in its broader aspects.

For example, a valve means in place of twist wire 44 can be secured to end portion 43 of liner bag 16 so that by manual operation, or by automatic operation, the valve means provides a sealed end portion 43 during the sterilizing cycle and provides a venting condition during the following flushing cycle. Venting may be provided by exhaust means 22 during the flush cycle and also upon completion of the flush cycle when the liner bag 16 is opened to thereby vent the residue sterilant gas within the liner bag 16.

What we claim is:

1. Apparatus for sterilizing articles in an enclosed area with a sterilant characterized by toxicity and flammability, said apparatus comprising a sealed first enclosure made at least partially of a gas-permeable plastic film, a sealed container for releasably containing a gaseous sterilant under pressure, said container being enclosed within said first enclosure, a second enclosure made at least partially of a gas-permeable plastic film, said second enclosure having an opening and means for partially closing said opening, the first enclosure and the articles to be sterilized being contained in said second enclosure, said first enclosure being constructed such that sterilant diffuses from said first enclosure into said second enclosure at a rate capable of establishing sterilization conditions in said second enclosure during a sterilization cycle to thereby effect sterilization of said articles in said second enclosure, a third enclosure in which the second enclosure containing the articles to be sterilized is disposed, a flushing means for introducing air into said second enclosure to flush out the sterilizing gas therein into said third enclosure during a flushing cycle following completion of said sterilization cycle, and exhaust means for exhausting said sterilant gas and air from said third enclosure during said flushing cycle and conducting said exhausted sterilant gas and air to a remote area outside of said enclosed area, whereby said flushing means and said exhaust means minimize the amount of residue sterilant gas in said enclosed area.

2. Apparatus according to claim 1, wherein said exhaust means comprises an exhaust fan having an air inlet, and exhaust conduit means between said air inlet and said third enclosure.

3. Apparatus according to claim 2, wherein said flushing means comprises an air pump having an air discharge outlet, and air conduit means between said air discharge outlet and the interior of said second enclosure.

4. Apparatus according to claim 1, wherein said air conduit means is disposed at least partially to said exhaust conduit means.

5. Apparatus according to claim 1, wherein said third enclosure is made of a rigid material, said third enclosure comprising a housing having an access door to introduce therein said second enclosure.

6. Apparatus according to claim 5, wherein said access door has a closed position spaced from said housing to pass ambient air into said third enclosure, said exhaust means being capable of maintaining a pressure less than atmospheric in said third enclosure during said sterilization and flushing cycles.

7. A method of sterilizing in an enclosed area comprising the steps of containing a volatile sterilant within a sealed first enclosure made at least partially of a gas-permeable plastic membrane, disposing said sealed first enclosure and the items to be sterilized within a second enclosure made at least partially of a gas-permeable plastic film, disposing said second enclosure within a third enclosure, effecting a sterilizing cycle by releasing the sterilant from said first container in gaseous form, passing said gaseous sterilant into said second enclosure by diffusion through said gas-permeable membrane, maintaining sterilizing conditions in said second enclosure to effect sterilization of said items to be sterilized in said second container, passing the gaseous sterilant from said second enclosure to said third enclosure by diffusion through said gas-permeable film, effecting a flushing cycle subsequent to said sterilizing cycle by introducing air into said second enclosure to flush out the sterilizing gas from said second enclosure into said third enclosure, exhausting said sterilizing gas and air from said third enclosure, and conducting said exhausted sterilizing gas and air to a remote area outside of said enclosed area, whereby said flushing cycle minimizes the amount of residue sterilant gas in said enclosed area.

8. A method according to claim 7 further comprising disposing said first, second, and third enclosures within a room of a building, said enclosed area being defined by said room, and conducting said exhausted sterilant gas and air to said remote area which is outside of said room.

9. A method according to claim 7 further comprising maintaining said third enclosure at a pressure less than atmospheric during said sterilization cycle.

10. A method according to claim 7 further comprising maintaining said third enclosure at a pressure less than atmospheric during said flushing cycle.

11. A method according to claim 7, wherein said second enclosure is made of an inflatable, gas-permeable, plastic film bag, said step of introducing air into said second enclosure comprising fully inflating said plastic film bag, and passing the sterilant gas and air in said inflated plastic film bag into said third enclosure through an opening in said plastic film bag.

12. A method according to claim 11 further comprising introducing said flushing air into said second enclosure through said opening in said plastic film bag.

13. A method according to claim 11, further comprising introducing said items to be sterilized into said second enclosure through said opening of said plastic film bag.

14. A method according to claim 7 further comprising effecting said flushing cycle for abut two hours.

15. A method according to claim 7, further comprising maintaining the level of concentration of residue sterilant gas in said enclosed area at less than 1 ppm.

16. A method according to claim 7, further comprising reducing the level of concentration of the residue sterilant gas in said second enclosure at the end of the flushing cycle to less than 1000 ppm.

17. Apparatus for sterilizing articles in an enclosed area with a sterilant characterized by toxicity and flammability, said apparatus comprising a sealed first enclosure made at least partially of a gas-permeable plastic film, a sealed container for releasably containing a gaseous sterilant under pressure, said container being enclosed within said first enclosure a second enclosure made at least partially of a gas-permeable plastic film, said second enclosure having an opening and means for partially closing said opening, the first enclosure and the articles to be sterilized being contained in said second enclosure, said first enclosure being constructed such that sterilant diffuses from said first enclosure into said second enclosure at a rate capable of establishing sterilization conditions in said second enclosure during a sterilization cycle to thereby effect sterilization of said articles in said second enclosure, a third enclosure in which the second enclosure containing the articles to be sterilized is disposed, a flushing means for introducing air through said opening into said second enclosure to inflate said second enclosure such that the introduced air and remaining sterilizing gas in said inflated second enclosure during a flushing cycle following completion of said sterilization cycle, and exhaust means for exhausting said sterilant gas and air from said third enclosure during said flushing cycle and conducting said exhausted sterilant gas and air to a remote air outside of said enclosed area, whereby said flushing means and said exhaust means minimize the amount of residue sterilant gas in said enclosed area.

18. Apparatus according to claim 17, wherein said flushing means comprises an air pump having an air discharge outlet, and air conduit means leading from said air discharge outlet and passing through said opening into the interior of said second enclosure.

19. A method of sterilizing in an enclosed area comprising the steps of containing a volatile sterilant within a sealed first enclosure made at least partially of a gas-permeable plastic membrane, disposing said sealed first enclosure and the time to be sterilized within a second enclosure made at least partially of a gas-permeable plastic film, disposing said second enclosure within a third enclosure, effecting a sterilizing cycle by releasing the sterilant from said first container in gaseous form, passing said gaseous sterilant into said second enclosure by diffusion through said gas-permeable membrane, maintaining sterilizing conditions in said second enclosure to effect sterilization of said items to be sterilized in said second container, passing the gaseous sterilant from said second enclosure to said third enclosure by diffusion through said gas-permeable film, effecting a flushing cycle subsequent to said sterilizing cycle by introducing air through an opening in said second enclosure into the interior of said second enclosure, inflating said second enclosure as a result of said introduced air, forcing the introduced air and remaining sterilizing gas in said inflated second enclosure to pass out of said opening into said third enclosure, exhausting said sterilizing gas and air from said third enclosure, and conducting said exhausted sterilizing gas and air to a remote area outside of said enclosed area, whereby said flushing cycle minimizes the amount of residue sterilant gas in said enclosed area.

* * * * *